United States Patent [19]
Seifter et al.

[11] Patent Number: 5,358,732
[45] Date of Patent: Oct. 25, 1994

[54] METHOD AND SYSTEM FOR REMOVING IMPURITIES FROM ALIMENTS

[75] Inventors: Eli Seifter, New Hyde Park; Jacques Padawer, Hastings-On-Hudson; Iraj Lalezari, Scarsdale, all of N.Y.

[73] Assignee: Albert Einstein College of Medicine of Yeshiva University, Bronx, N.Y.

[21] Appl. No.: 105,024

[22] Filed: Aug. 10, 1993

[51] Int. Cl.$^5$ .......................... A23L 1/015; C12G 3/08
[52] U.S. Cl. ................................. 426/592; 426/425; 426/429; 426/430; 426/431; 426/432; 426/478; 426/479; 426/486; 426/487; 426/488; 426/493; 426/573; 210/638
[58] Field of Search ............ 426/592, 330.4, 573, 426/425, 429, 430, 431, 432, 478, 479, 486, 487, 488, 493; 210/638

[56] References Cited

U.S. PATENT DOCUMENTS

| | | | |
|---|---|---|---|
| 2,500,183 | 3/1950 | Hulsman | 426/592 |
| 3,958,023 | 5/1976 | Butterworth | 426/330.4 |
| 4,844,911 | 7/1989 | Kakimoto et al. | |
| 4,936,999 | 6/1990 | Mattison et al. | 210/651 |
| 5,000,966 | 3/1991 | Sumino et al. | |

*Primary Examiner*—Helen Pratt
*Attorney, Agent, or Firm*—Amster, Rothstein & Ebenstein

[57] ABSTRACT

A method for improving the quality of an aliment, such as an alcoholic liquor, by removing impurities such as carbamates, sulfites and bioamines, includes contacting an aliment containing the impurity with a container formed of a membrane permeable to the impurity. The container encloses a non-diffusible reactant such as binding agents, neutralizing agents, oxidizing agents, transesterifying agents and hydrolyzing agents. The container and the contents are separated from the aliment after a period of time sufficient for the reactants to react with the impurity.

23 Claims, 8 Drawing Sheets

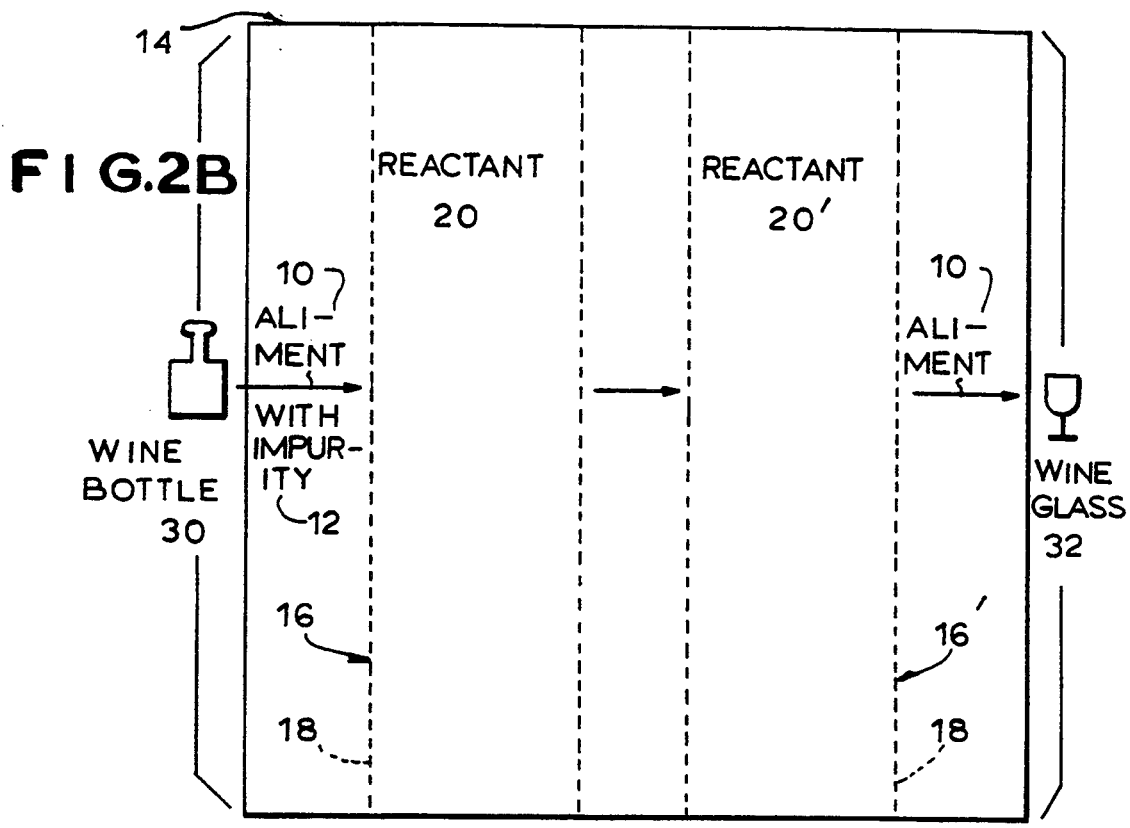
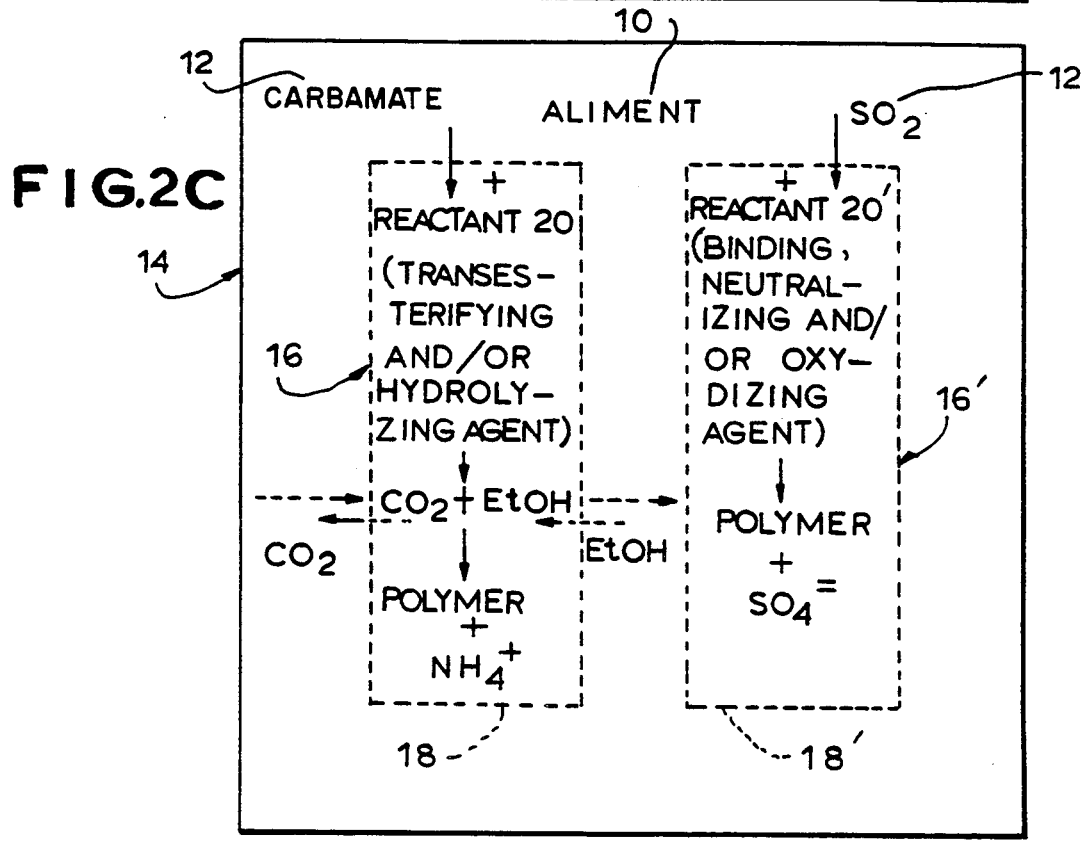

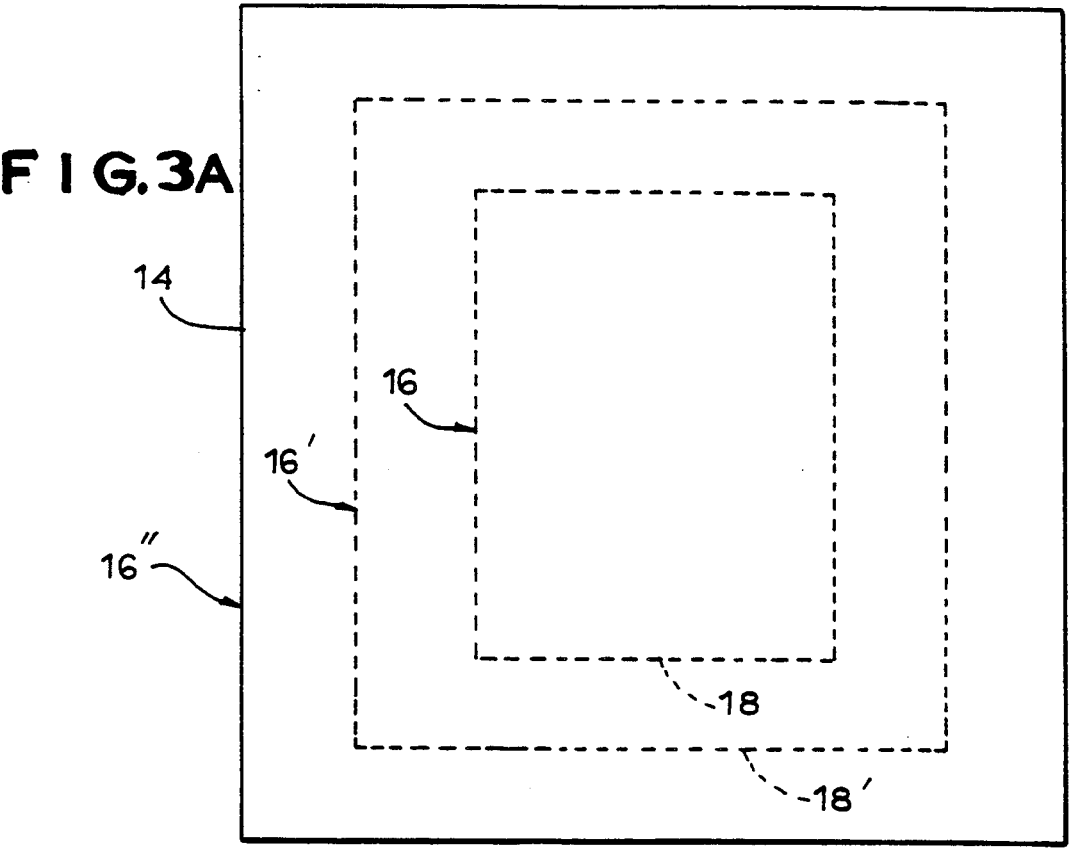
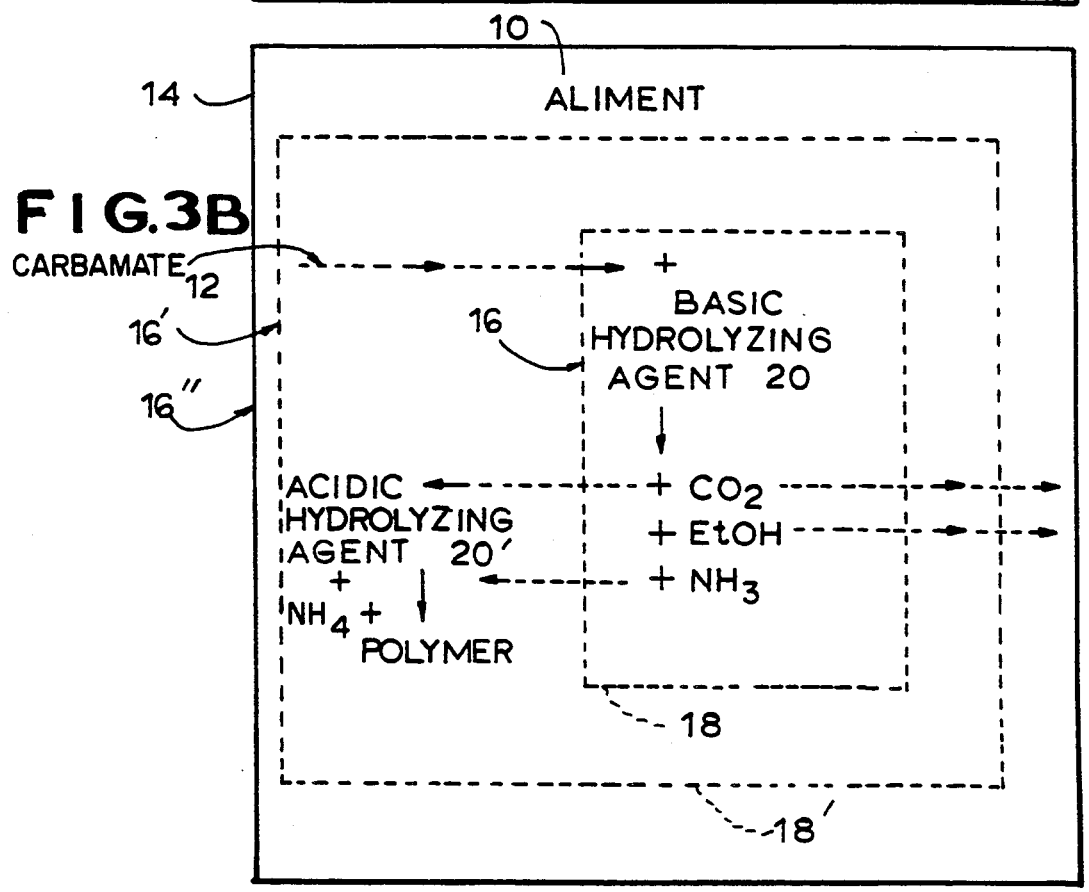

METHOD AND SYSTEM FOR REMOVING IMPURITIES FROM ALIMENTS

BACKGROUND OF THE INVENTION

The present invention relates to a method for improving the quality of an aliment, such as an alcoholic liquor, by removing therefrom an impurity, and more particularly to such a method for use where the impurity is a carbamate, sulfite or bioamine.

Urethan (also known as urethane, carbamic acid ethyl ester, ethylcarbamate, etc.) is a common carbamate in beers and wines. It is a naturally occurring product of yeast fermentations and arises from the reaction of various carbamoyl compounds and enzymatically-produced ethanol. These reactions account for most of the urethan present in beers and wines. Urethan may also be generated during the aging of wines and beers as a result of interactions of these beverages with the structural materials of the barrels and vats in which they are stored, often for long periods of time. Urethan is also present in distillates of beers and wines, some of that urethan arising from chemical interactions between ammonia, carbon dioxide and ethanol at the elevated temperatures required for the economic production of distilled beverages.

Urethan is now considered by the Environmental Protection Agency of the United States as a cancer suspect or carcinogenic agent, and urethan levels in beverages are regulated in several countries. For example, current regulations in the U.S. restrict its acceptable concentrations to 10 ppb (parts per billion) for table wines or 14 ppb for fortified wines. While there is some uncertainty as to whether urethan is itself the ultimate carcinogen or whether its metabolites or oxidation products are the carcinogenic agents, the further reduction, or ideally the total elimination, of urethan is considered highly desirable, but is limited by the available economically feasible technologies for doing so.

By way of background, the prior art suggests the removal of urethan precursors from beverages, for example, by treatment with urease enzyme to hydrolyze the precursors into ammonia and carbon dioxide, thereby to prevent urethan from being formed during the heating of the precursors and ethanol during pasteurization. However, the urease enzyme is inhibited by phenols, such as those frequently present in mashes from both grains and grapes, by ethanol (a desired fermentation product) and by sulfur dioxide (a natural constituent of beers and wines resulting from the fermentation of yeast and frequently present in wines as a result of the means used to decontaminate the barrels and vats used during fermentation). Additionally, the enzymes are rarely totally pure and frequently contain by-products which affect bouquet, taste and the like, and may even, if insufficiently purified, contain harmful bacteria therein. Urethan is a particular problem in connection with distilled alcoholic beverages, as much urethan is formed during the distillation process itself in addition to the smaller amounts generated during fermentation. Because they contain carbamoyl compounds, beers or mashes of necessity contain high amounts of the very reactants which produce urethan: ammonia, carbon dioxide, and ethyl alcohol.

Other undesirable carbamates frequently present as a food or liquid contaminant include the N-methyl carbamates used in pesticides and fungicides.

The term "sulfites" as used herein includes the salts of sulfurous acids ($M_2SO_3$), acid-sulfites ($MHSO_3$, also known as bisulfites), sulfur dioxide ($SO_2$, also known as sulfurous acid anhydride), metabisulfites ($M_2S_2O_5$), hydrosulfites ($M_2S_2O_4$) and the like. Storage kegs often are sterilized with burning sulfur candles, and the resulting sulfite can find its way from the keg into hard liquors to which it is not added purposefully. Sulfites are intentionally used extensively in the treatment of alcoholic beverages (such as wines) and some frozen vegetables as well as in the treatment of foods and non-alcoholic beverages (such as some fruit juices). The sulfites are used as color stabilizers and as preservatives to preserve the products against spoilage due to bacteria and fungi. Wines contain about 3 ppm (parts per million) sulfur dioxide produced by yeast metabolism and additionally up to 30 ppm of sulfites added purposefully during wine making. While some of the actions of the sulfites are highly desirable (e.g., color stabilization, preservation, and the like), many of the sulfite actions are highly negative (e.g., allergic reactions with occasional consequent deaths, inactivation of particular protein-carbohydrate linkages, bronchial constriction and irritation, possible carcinogenicity, and the like). While U.S. government regulations require wines sold in the U.S. which contain more than 10 ppm equivalents to be labeled as "contains sulfites", there is great pressure to continue the use of sulfites in the wine industry as a color stabilizer and preservative.

The term "bioamines" as used herein includes the various organic amines such as tyramine, histamine, methylpropylamine and phenethylamine. Bioamines are believed to be a significant factor in the development of a "hangover" after alcohol has been consumed, especially in the form of wines. Additionally, the bioamines naturally present in fish (e.g., choline and trimethylamine) are a significant factor in the production of the characteristic fishy smell associated with stored or frozen then thawed fish. Thus there are clear advantages to the removal of bioamines from various aliments.

While the desirability of removing carbamates, sulfites, bioamines and like impurities from various aliments (e.g., solid foods, alcoholic and non-alcoholic beverages, ingestible fluids, drugs and the like intended to be taken internally) appears obvious, the requirements imposed upon the agents used to remove the same are manifold and arduous. To be acceptable, such an agent must be economical to use, have a very high affinity for the impurity, be insoluble in the beverage, not contribute any substances of its own to the beverage, and be inert in terms of affecting the color, taste or composition of non-offending substances in the beverage.

The term "aliment" as used herein refers to a substance taken into the body and includes both low alcohol, high alcohol, and non-alcohol beverages (e.g., fruit juices) as well as solid foods (whether frozen or not), drugs (whether ingested or injected) and the like. For solid foods, sulfites and bioamines are a major problem, while carbamates are not. For drugs, sulfites are a major problem but, since they are used to stabilize drugs, they are preferably not removed until immediately prior to use either by ingestion or injection. The preferred late removal of sulfites from drugs thus parallels its preferred late removal from various foods and beverages where its stabilizing effects are desired until just prior to consumption.

The term "impurity" as used herein refers to any undesriable or unwanted component of the aliment, whether naturally occurring or added for some purpose.

Accordingly, an object of the present invention is to provide method for improving the quality of an aliment by removing at least one impurity therefrom.

Another object is to provide such a method for improving the quality of an alcoholic liquor by removing therefrom an impurity.

A further object is to provide such a method for improving the quality of an aliment by removing an impurity selected from the group consisting of carbamates, sulfites, bioamines and combinations thereof.

It is also an object to provide such a method which economically removes the impurity without degrading the quality of the aliment.

SUMMARY OF THE INVENTION

It has now been found that the above and related objects of the present invention are obtained in a method for improving the quality of an aliment such as an alcoholic liquor by removing therefrom an impurity selected from the group consisting of carbamates, sulfites, bioamines, and combinations thereof. The method comprises the steps of contacting an aliment containing an impurity selected from the group consisting of carbamates, sulfites, bioamines, and combinations thereof, with a container formed of a membrane permeable to the impurity or its breakdown products and enclosing a reactant non-diffusible through the membrane. The reactant is selected from the group consisting of a binding agent, a neutralizing agent, an oxidizing agent, a transesterifying agent, a hydrolyzing agent, and combinations thereof. The container and the contents thereof are separated from the aliment after a period of time sufficient for the reactant to react with the impurity.

In a first preferred embodiment, the present invention encompasses a method for improving the quality of an aliment (such as an alcoholic liquor, food or drug) by removing therefrom sulfites. The method comprises the steps of contacting an aliment containing sulfites with a container formed of a membrane permeable to sulfites and their breakdown products (e.g., sulfur dioxide) and enclosing a non-diffusible reactant. The reactant is selected from the group consisting of a binding agent including a non-diffusible polymeric aldehyde for binding sulfites into a non-diffusible polymer sulfite complex, a neutralizing agent including a non-diffusible polymeric base for neutralizing sulfites, an oxidizing agent including a non-diffusible peroxide for oxidizing sulfites to sulfates, and combinations thereof. The container and the contents thereof are separated from the aliment after a period of time sufficient for the reactant to react. Optionally the container further encloses an antioxidant including a non-diffusible polymeric phenol for maintaining the reduced forms of natural phenols.

In a second preferred embodiment, the present invention encompasses a method for improving the quality of an aliment (such as an alcoholic liquor) by removing therefrom carbamates. The method comprises the steps of contacting an aliment containing carbamate with a container formed of a membrane permeable to carbamate and its breakdown products and enclosing a non-diffusible reactant. The reactant is selected from the group consisting of a transesterification agent including a non-diffusible polymer containing hydroxyphenyl moieties for reacting with carbamates to form a non-diffusible hydrolyzable aryl ester of carbamic acid, an acidic hydrolyzing agent including a non-diffusible strongly acidic polymer for hydrolyzing carbamates and binding the ammonia by-product, a basic hydrolyzing agent including a non-diffusible strongly basic polymer for hydrolyzing carbamates, an enzymatic hydrolyzing agent including a non-diffusible esterolytic enzyme for hydrolyzing carbamates, and combinations thereof. The container and the contents thereof are separated from the aliment after a period of time sufficient for the reactant to react.

In a third preferred embodiment, the present invention encompasses a method of improving the quality of an aliment (such as wines and fish) by removing therefrom bioamines. The method comprises the steps of contacting an aliment containing bioamines with a container formed of a membrane permeable to bioamines and their breakdown products and enclosing a non-diffusible reactant. The reactant is a binding agent selected from the group consisting of a non-diffusible polymeric aldehyde, a strongly acidic resin, and combinations thereof. The container and the contents thereof are separated from the aliment after a period of time sufficient for the reactant to react.

Generally the present invention encompasses a method for improving the quality of an aliment by removing therefrom an impurity. The method comprises the steps of contacting an aliment containing an impurity with a container formed of a membrane permeable to the impurity and its breakdown products and enclosing a reactant non-diffusible through the membrane. The reactant is selected from the group consisting of a binding agent, a neutralizing agent, an oxidizing agent, a transesterifying agent, a hydrolyzing agent, and combinations thereof. The container and the contents thereof are separated from the aliment after a period of time sufficient for the reactant to react with the impurity.

The present invention also encompasses a system for improving the quality of an aliment by removing therefrom at least one impurity selected from the group consisting of carbamates, sulfites and bioamines. The system comprises a liquid-impermeable vessel enclosing an aliment containing an impurity selected from the group consisting of carbamates, sulfites, bioamines and combinations thereof, and in fluid communication with the aliment, a container formed of a membrane permeable to the impurity and its breakdown products. The membrane encloses a reactant non-diffusible through the membrane and selected from the group consisting of a binding agent, a neutralizing agent, an oxidizing agent, a transesterifying agent, a hydrolyzing agent, and combinations thereof.

In a first preferred embodiment, the present invention encompasses a system for improving the quality of an aliment by removing therefrom sulfites. The system comprises a liquid-impermeable vessel enclosing an aliment containing sulfites, and, in fluid communication with the aliment, a container formed of a membrane permeable to sulfites and enclosing a non-diffusible reactant selected from the group described above with regard to sulfite removal.

In a second preferred embodiment, the present invention comprises a system for improving the quality of an aliment by removing therefrom carbamates. The system comprises a liquid-impermeable vessel enclosing an aliment containing carbamate, and, in fluid communication with the aliment, a container formed of a membrane permeable to carbamate and enclosing a non-diffusible reactant selected from the group described above with regard to carbamate removal.

In a third preferred embodiment, the present invention encompasses a system for improving the quality of an aliment by removing therefrom bioamines, the system comprises a liquid-impermeable vessel enclosing an aliment containing bioamines, and, in fluid communication with the aliment, a container formed of a membrane permeable to bioamines and enclosing the non-diffusible reactant described above for removal of bioamines.

More generally, the present invention encompasses a system for improving the quality of an aliment by removing therefrom at least one impurity. The system comprises a liquid-impermeable vessel enclosing an aliment containing an impurity, and, in fluid communication with the aliment, a container formed of a membrane permeable to the impurity and its breakdown products and enclosing a reactant non-diffusible through the membrane and selected from the group consisting of a binding agent, a neutralizing agent, an oxidizing agent, a transesterifying agent, a hydrolyzing agent, and combinations thereof.

Preferably the system includes a plurality of the containers, the containers being separate and distinct, especially where the reactants of at least two of the plurality of containers are incompatible. Alternatively, the system includes a stacked plurality of the containers, an inner one of the containers being disposed entirely within an outer one of the containers, especially where the reactants of at least two of the plurality of containers are incompatible. For example, the inner container encloses an acidic hydrolyzing agent and the outer container encloses a basic hydrolyzing agent, the membrane intermediate the inner and outer containers being permeable to carbamate, ammonia, carbon dioxide and ethanol.

Where the vessel defines an open top, the container is removably disposed on the vessel to close the open top. Where the container substantially encloses the vessel, the vessel defines a porous hydrophobic vent. Where the vessel substantially encloses the container, each of the vessel and the container defines a porous hydrophobic vent.

BRIEF DESCRIPTION OF THE DRAWING

The above and related objects, features and advantages of the present invention will be more fully understood by reference to the following detailed description of the presently preferred, albeit illustrative, embodiments of the present invention when taken in conjunction with the accompanying drawing wherein:

FIG. 2B is a schematic view illustrating the use of the second embodiment to remove impurities immediately prior to consumption of the aliment;

FIG. 2C is a schematic view of the second embodiment as used to remove both carbamates and sulfites;

FIG. 3A is a general schematic view of a third embodiment of the present invention wherein one container is stacked within another container within the vessel;

FIG. 3B is a schematic view illustrating the use of the third embodiment for the removal of carbamates with two incompatible agents.

DETAILED DESCRIPTION OF THE PREFERRED EMBODIMENTS

According to the present invention, the method for improving the quality of an aliment, especially a beverage such as an alcoholic liquor (whether beer, wine, or hard liquor) by removing therefrom an impurity selected from the group consisting of carbamates, sulfites, bioamines, and combinations thereof, relies upon membrane technology. It will be appreciated that the purification processes described hereinbelow are not for the purposes of preventing formation of the impurities, but rather to lower the impurity content, once formed, by removing them from the aliment or beverage. For example, the carbamates are decomposed, the sulfites are either decomposed or bound, and the bioamines are bound.

A large technology has developed based upon membrane usage to concentrate solvents such as water (for example, in desalination efforts), low molecular weight solutes such as salts or high molecular weight solutes such as proteins. Selected action of such membranes is based upon the size of the pores in the membranes, either alone or as modified by permeability-altering coatings supported by the membranes. The net rate at which materials move or diffuse across a barrier (e.g., the membrane) from a region of higher concentration into an area of lesser concentration is dependent upon the number of molecules in the diffusing chemical that contact or collide with each side of the membrane over time. This is dependent mainly on the concentration of the diffusing chemical on each side of the membrane and, more specifically, on the difference in concentration or concentration gradient. This, in turn, may depend upon the temperature and pressure applied on each side of the membrane (i.e., the temperature and pressure gradients) or the activity of the diffusing chemical. In addition, diffusion is dependent on various intrinsic factors such as molecule size, charge, hydration and other factors that contribute to the diffusion constant.

Figure 1A:
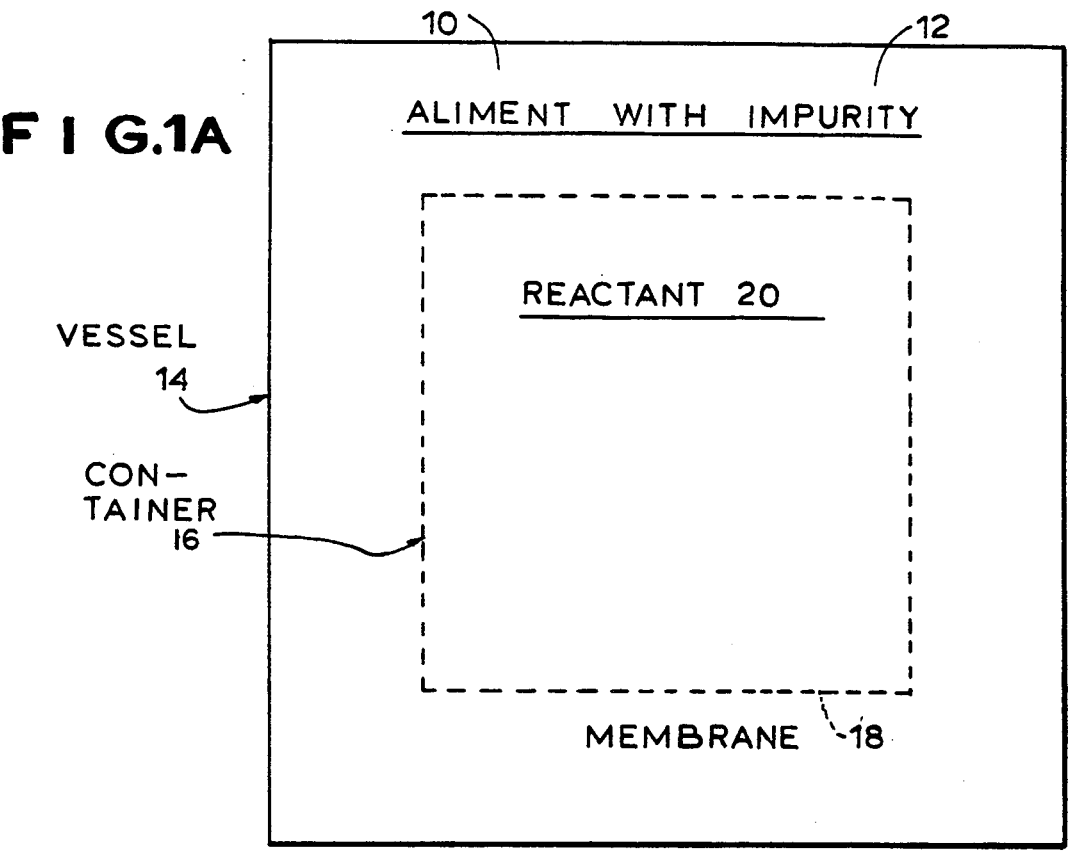
FIG. 1A is a general schematic view of a first embodiment of the present invention wherein there is a single compartment within the vessel.

Referring now to FIG. 1A, therein illustrated is a general schematic of the first or "single container in a vessel" embodiment of the present invention. An aliment (such as an alcoholic beverage), generally designated by the reference numeral 10, contains the impurity 12 carbamate) to be removed and is disposed in a fluid-impermeable vessel generally designated 14 in fluid contact with a container generally designated 16. The fluid-impermeable vessel 14 may be formed of glass, ceramic, plastic (such as polycarbonate), or treated or lined wood, provided that the vessel 14 does not leak or permit loss of its aliment or gaseous contents to the environment except by the deliberate use of vents or taps.

The container 16 is formed of a membrane 18, which is permeable to the impurity 12 to be removed so that the impurity 12 can diffuse from the aliment 10 into container 16. Thus, where the impurity 12 is a carbamate, a sulfite, or a bioamine, the membrane 18 must be permeable to the carbamate, the sulfite, or the bioamine, respectively. Typically the membrane 18 will not be permeable to each of the possible sulfites which may be present in the aliment 10. However, as long as the membrane 18 is permeable to sufur dioxide ($SO_2$), it will be considered as permeable to the sulfites for the purposes of the present invention since the sulfur dioxide is in equilibrium with the sulfites and, as the sulfur dioxide passes through the membrane, the remaining sulfites will tend to break down to produce more sulfur dioxide. Where a plurality of impurities are to be removed, then the membrane 18 must be permeable to the plurality of impurities. Where the impurity is to be hydrolyzed or otherwise treated to form breakdown products, the membrane 18 must be permeable to the breakdown products, thereby to prevent an accumulation of the breakdown products within the container 16 which might adversely affect the equilibrium point of the reactions proceeding therewithin.

The membrane 18 may be in the form of an amorphous sack or a structured configuration. The membrane 18 encloses at least one reactant 20 appropriate for the impurity 12 to be removed and non-permeable through the membrane 18. The aforementioned non-diffusible reactant 20 reacts with the impurity 12 to irreversibly form a complex which is itself non-diffusible and thus cannot cross the membrane 18, thereby preventing the back-diffusion of the impurity 12 from the compartment 16 back into the aliment 10 of the vessel 14 and thus lowering the effective concentration of the impurity 12 on the side of the membrane with the lesser impurity concentration. The reactant 20 can either be loose within the compartment 16 or affixed to the inner surface of the membrane 18.

After a period of time sufficient for the reactant 20 to react with the impurity 12 to be removed, the container 16 and the contents thereof are separated from the aliment 10.

Thus, for sulfite impurities, the reactant may be a binding agent including a non-diffusible polymeric aldehyde for binding sulfites in non-diffusible polymers (that is, polymers that cannot diffuse through the membrane), a neutralizing agent including a non-diffusible polymeric base for neutralizing sulfites, or an oxidizing agent including a non-diffusible peroxide for oxidizing sulfites (which are diffusible through a hydrophobic membrane as $SO_2$) to sulfates (which are non-diffusible through a hydrophobic membrane), or a combination thereof.

More particularly, the non-diffusible polymeric aldehyde for binding sulfites into a non-diffusible polymer may utilize the polymeric aldehydes derived by periodic acid treatment of natural carbohydrate polymers (such as from starch, starch dialdehydes, cellulose, xylosans, polygalactans, dextrins, agarose, or the like). Chemically modified carbohydrates (such as dimethylaminoethylated cellulose, partially carboxymethylated cellulose or the like) may similarly be converted to aldehydes having both binding and neutralizing properties. The non-diffusible polymeric bases for neutralizing sulfites are preferably aminomethyl and aminoethyl ether derivatives of starch or cellulose (such as dimethylaminoethyl cellulose and aminoethyl cellulose) and aminomethyl derivatives of polystyrene (e.g., cholestyramine and poly[aminoethyl]polystyrene) or the like. The polymeric base may be either strongly or weakly basic provided that it exchanges its hydroxyl anion for a sulfite moiety. (Instead of the polymeric base or alkaline polymer, a solution may be rendered alkaline with excess hydroxides or carbonates (e.g., CaO, MgO, $CaCO_3$, $MgCO_3$, $Al_2O_3$, silicates, etc.) providing that the membrane is hydrophobic. Excess $CaCO_3$ may be used to trap the $SO_2$ within a hydrophobic container and thereby promote passage of $SO_2$ from the aliment into the container.) The non-diffusible peroxide for oxidizing sulfites to sulfates is preferably dilute hydrogen peroxide and may be used in conjunction with a hydrophobic membrane either alone or in combination with an alkaline carbonate or hydroxide to produce an insoluble and non-diffusible sulfate upon reaction with the sulfite. Low levels of stabilized peroxides (e.g., $H_2O_2$-polyvinylpyrrolidone complex) are also effective, but only with a phobic membrane to prevent diffusion of low molecular weight fractions and to avoid osmotic effects with higher molecular weight fractions.

The container may also enclose an antioxidant including a non-diffusible polymeric phenol for maintaining the reduced forms of natural phenols in beer and wines, thereby to maintain a natural color and clarity. The non-diffusible polymeric phenols for this purpose are preferably lignin and Baekelite. These compounds also act as transesterification agents and form addition products with $SO_2$.

For carbamate impurities, the reactant may be a transesterifying agent including a non-diffusible polymer containing hydroxyphenyl moieties for reacting with carbamate to form a non-diffusible hydrolyzable aryl ester of carbamic acid, an acidic hydrolyzing agent including a non-diffusible, strongly acidic polymer for hydrolyzing carbamate and binding the ammonia by-product, a basic hydrolyzing agent including a non-diffusible strongly basic polymer for hydrolyzing carbamate, an enzymatic hydrolyzing agent including a non-diffusible esterolytic enzyme, or a combination thereof.

More particularly, the non-diffusible polymer for reacting with carbamates, to form a non-diffusible hydrolyzable aryl ester of carbamic acid, contains hydroxyphenyl moieties (e.g., phenols) which react with carbamate to produce carbamyl phenols or other non-diffusible hydrolyzable aryl esters of carbamic acid plus ethanol and carbon dioxide. The polymer may be natural or synthetic, and soluble or insoluble. Preferred polymers include polyphenols, purified lignin and phenolaldehyde copolymers (e.g., Baekelite). The aryl esters of carbamic acid are less stable than their alkyl counterparts and thus very readily hydrolyzed to ammonia, carbon dioxide and the regenerated polyphenol. Under some conditions, the polyphenols may serve to stabilize the color, bouquet and flavor of the beverage due to their antioxidant action. The preferred polyphenols are lignin and Baekelite.

The non-diffusible strongly acidic polymer for hydrolyzing carbamates and binding the ammonia by-product is preferably a sulfonated polystyrene or its homologs (e.g., sulfonic acid resin, polystyrene sulfonic acid, polyethanolsulfonic acid, or sulfonated lignin). Urethan diffusing across the membrane is hydrolyzed by the acidic polymer to ammonia, carbon dioxide and ethanol, the ammonia becoming fixed by the acidic polymer and thereby rendered non-diffusible through the membrane.

The non-diffusible strongly basic polymer is preferably a polymeric quaternary ammonium hydroxide or a poly(trimethylamino)-polystyrene. While the strongly basic polymer is able to hydrolyze the carbamate in the same manner as the strongly acidic polymer, the strongly basic polymer is not able to fix the ammonia. Accordingly, a trapping agent for the ammonium ion, such as a non-diffusible acidic polymer, is often used with the basic polymer but the two must be separated by a membrane.

The rate and extent of hydrolysis will be dependent upon the concentration of $H^+$ for the acidic polymers and $OH^-$ for the basic polymers. (Note that the use of simple strong acids or bases to hydrolyze the carbamate is typically not feasible, as the simple strong acids or bases themselves would diffuse through the typically hydrophilic membrane and contaminate the aliment. On the other hand, typically the sulfite removal process employs a hydrophobic membrane which is non-permeable to the simple strong acids or bases.) Weakly acidic polymers (e.g., polyacrylic acids) and weakly basic polymers (e.g., tertiary amines) are not as effective in causing hydrolysis as are their stronger counterparts, nor is the weakly acidic polymer as effective in binding the ammonia by-product as the strongly acidic polymer. Nonetheless, acidic polymers which are less than strongly acidic and basic polymers which are less than strongly basic may be of value in particular instances, especially where combined with other agents such as the transesterifying agents discussed above. The nitrogen-containing by-product of the carbamate hydrolysis is ammonia in a basic solution or ammonium ion (e.g., ammonium salt) in an acidic solution.

The non-diffusible esterolytic enzyme for hydrolyzing carbamates is preferably a pancreatic lipase or esterase.

For bioamine impurities, the reactant is a binding agent including a non-diffusible polymeric strong acid or aldehyde resin for binding bioamines into a non-diffusible polymer. More particularly, the strong acid binding agent may include a polysulfonic or polysulfate acidic resin for binding the basic or cationic components of the bioamine, and the aldehyde binding agent may include a starch or cellulose polyaldehyde.

It will be appreciated that certain of the reactants may fall into more than one of the categories described above. Thus starch polyaldehyde and cellulose dialdehyde derivatives are both neutralizing agents and binding agents, and some of the mentioned aminomethyl derivatives of polystyrene are also strong hydrolyzing agents. For instance, cholestyramine, a polystyrene trimethylbenzylammonium hydroxide resin, is a neutralizing agent (a strongly basic resin), a binding agent (its cationic amino groups bind anionic sulfite), and a hydrolyzing agent. Polysulfonic resin is a neutralizing agent, a hydrolyzing agent, and a transesterification agent (namely, a catalyst). On the other hand, it will be appreciated that some of the reactants may not be enclosed within the same container without interfering with the function of at least one of the reactants. Thus a strong acid hydrolyzing agent and a strong basic hydrolyzing agent cannot be combined in the same container, as they will neutralize one another prior to the introduction of the impurity they are designed to hydrolyze. Accordingly, in certain instances the first embodiment of the membrane system is not suitable and one of the other embodiments thereof must be used—e.g., an embodiment wherein there are provided at least two separate compartments, with, for example, the acidic hydrolyzing agent being disposed in one component and the basic hydrolyzing agent being disposed in another compartment.

The hydrophobic membranes are preferably polyethylene, polypropylene, polystyrene, [poly]fluorinated polypropylene, polyvinyl chloride, polyvinylidene chloride, polymethylsilane, polybutadiene, polymerized perfluoropropylene or perfluoroethylene, elastomers containing natural or synthetic rubber, or even hydrophilic membranes treated with silicones to provide a hydrophobic nature. The hydrophilic membranes are preferably cellulosic derivatives such as membranes of regenerated cellulose, alkylcellulose or a stable ester of cellulose (e.g., rayon) which can be either hydrophilic or hydrophobic depending on modification. For instance, partial acylation yields hydrophilic membranes, but complete acylation of cellulose yields hydrophobic membranes.

Choice of philic or phobic membranes depends on the application at hand. For instance, carbamate will cross faster through a hydrophilic membrane if the system is primarily aqueous, e.g., at low alcohol concentrations, but faster through hydrophobic membranes if the system is essentially alcoholic, e.g., at high alcohol concentration. For removal of carbamate from a venerable cognac of Napoleon after decorking the bottle, one needs rapid removal. Thus the choice of membrane type is critical as only seconds may be available for carbamate removal as the cognac is being poured. But for liquor sealed in bond today for storage until the next decade, time is not a factor, and the choice of membrane type is not critical.

To remove trace and small amounts of carbamate from an essentially aqueous solution containing 3–21% alcohol (about the concentration of alcohol in beers and wines), hydrophilic membranes such as cellulose are generally preferred as they are readily permeable to carbamate and provide higher membrane diffusion rates. A water-permeable membrane such as regenerated cellulose may be used. On the other hand, for essentially non-aqueous solutions (such as whiskies and other high-alcohol-content beverages having alcohol contents of between 40% and 80%), hydrophobic membranes are generally preferred for higher membrane diffusion rates. Hydrophilic membranes may be used in the hydrolysis and binding of carbamates in aqueous systems.

When the hydrophilic membranes are used for sulfite removal, care must be taken to use non-diffusible polyaldehydes or polyamines to prevent back-diffusion or possible contamination of the aliment with the trapping agent. While hydrophilic membranes will pass sulfites (including sulfur dioxide), hydrophobic membranes will pass sulfur dioxide but not the other sulfites.

Notwithstanding the general rules of preference set forth above regarding the choice of philic or phobic membranes, the general rules must give way to the specific requirements of a particular membrane system. Thus, where the reactant is a strong acidic or basic low molecular weight hydrolyzing agent, a hydrophobic membrane must be used to enclose the reactants in order to prevent diffusion of the hydrolyzing agent into the aliment. The particular factors which will determine whether or not a membrane must be either hydrophobic or hydrophilic will be readily evident to chemists, and particularly chemists familiar with membrane technology, so that a lengthy enumeration of the various situations wherein one or another type of membrane is required need not be set forth herein.

Figure 1B:
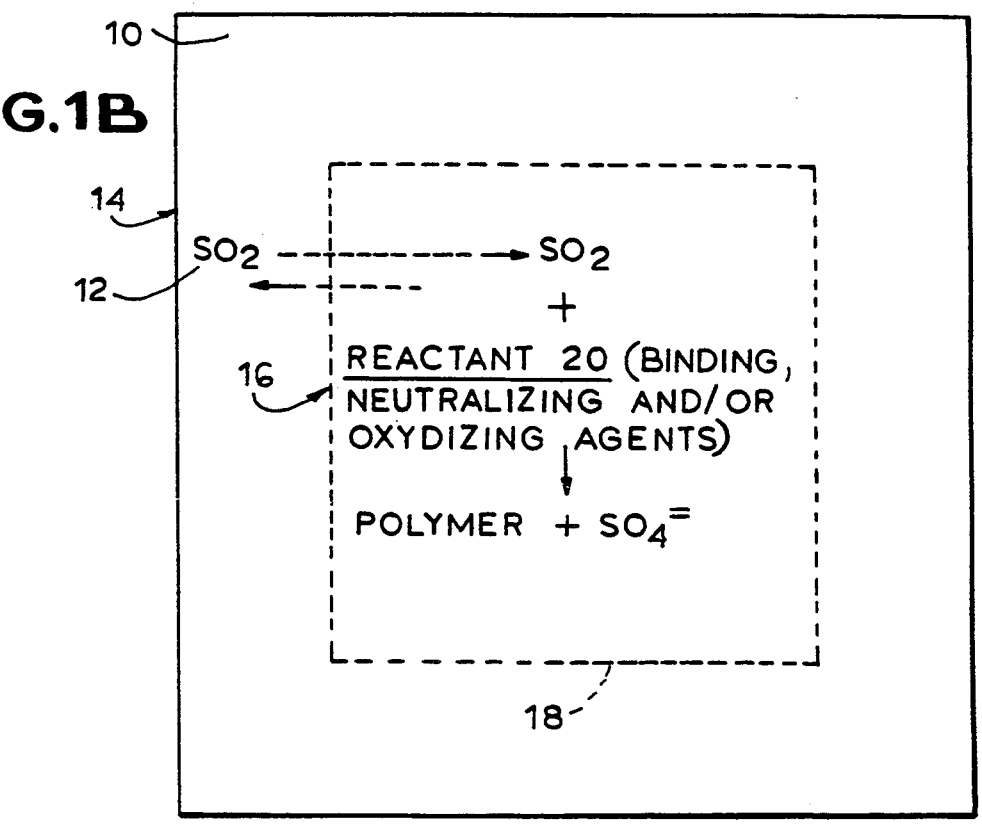
FIGS. 1B, 1C and 1D are schematic views showing the first embodiment as used for the removal of sulfites, carbamates, and bioamines respectively.

Referring now to FIG. 1B, therein illustrated is a schematic of the first embodiment of the present invention for the removal of sulfites 12 from the aliment 10 using binding, neutralizing and/or oxidizing agents 20. The reaction products formed—primarily polymers and sulfate—are non-diffusible through the membrane 18 and thus remain trapped within the container 16. An oxidizing agent may be used to remove sulfites (by oxidizing them to sulfates) only where a hydrophobic membrane is used so that the sulfates produced cannot back-diffuse.

Figure 1C:
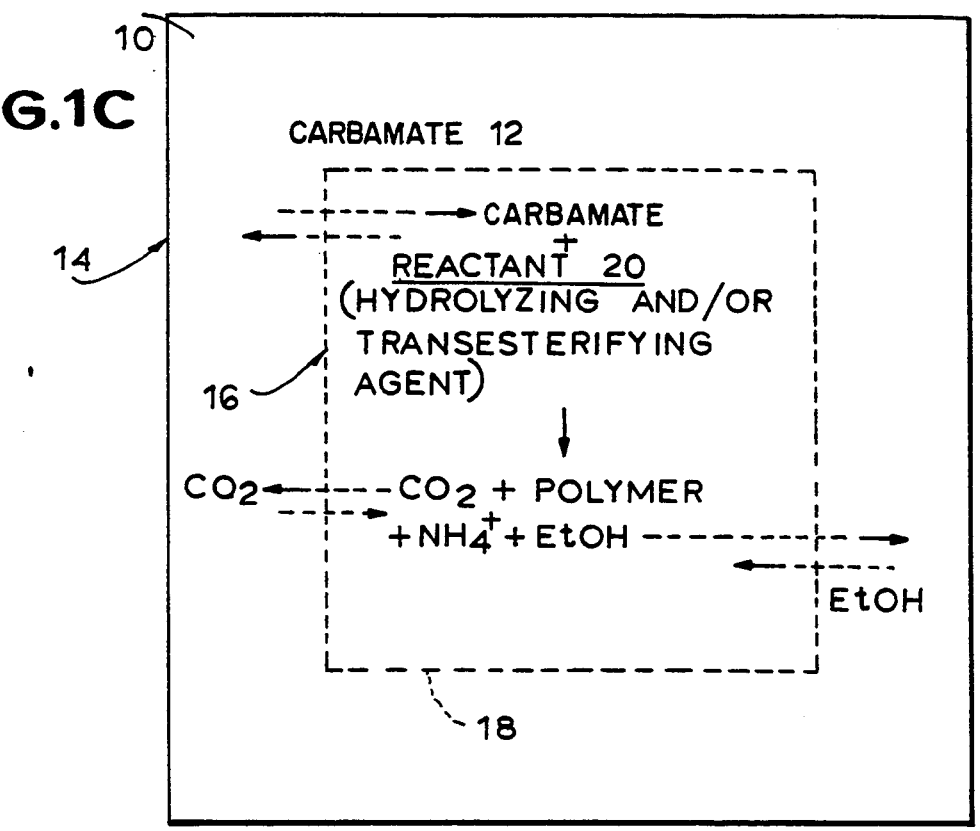

Referring now to FIG. 1C, therein illustrated is a schematic of the first embodiment of the present invention as used for the removal of carbamates 12 from the aliment 10 using transesterifying and/or hydrolyzing agents 20 (whether acidic, basic, or enzymatic hydrolyzing agents). The breakdown products carbon dioxide and ethyl alcohol can readily diffuse through the membrane 18, but produce no adverse effect on the aliment 10, while the trace amounts of ammonia or ammonium breakdown product are preferentially trapped within the container 16 (for example, by an acidic hydrolyzing agent or a trapping agent such as a non-diffusible, acidic polymer) so that it is not added to the aliment. The polymers and the trapped ammonia or ammonium ion remain within the container, as they cannot diffuse through membrane 18.

Figure 1D:
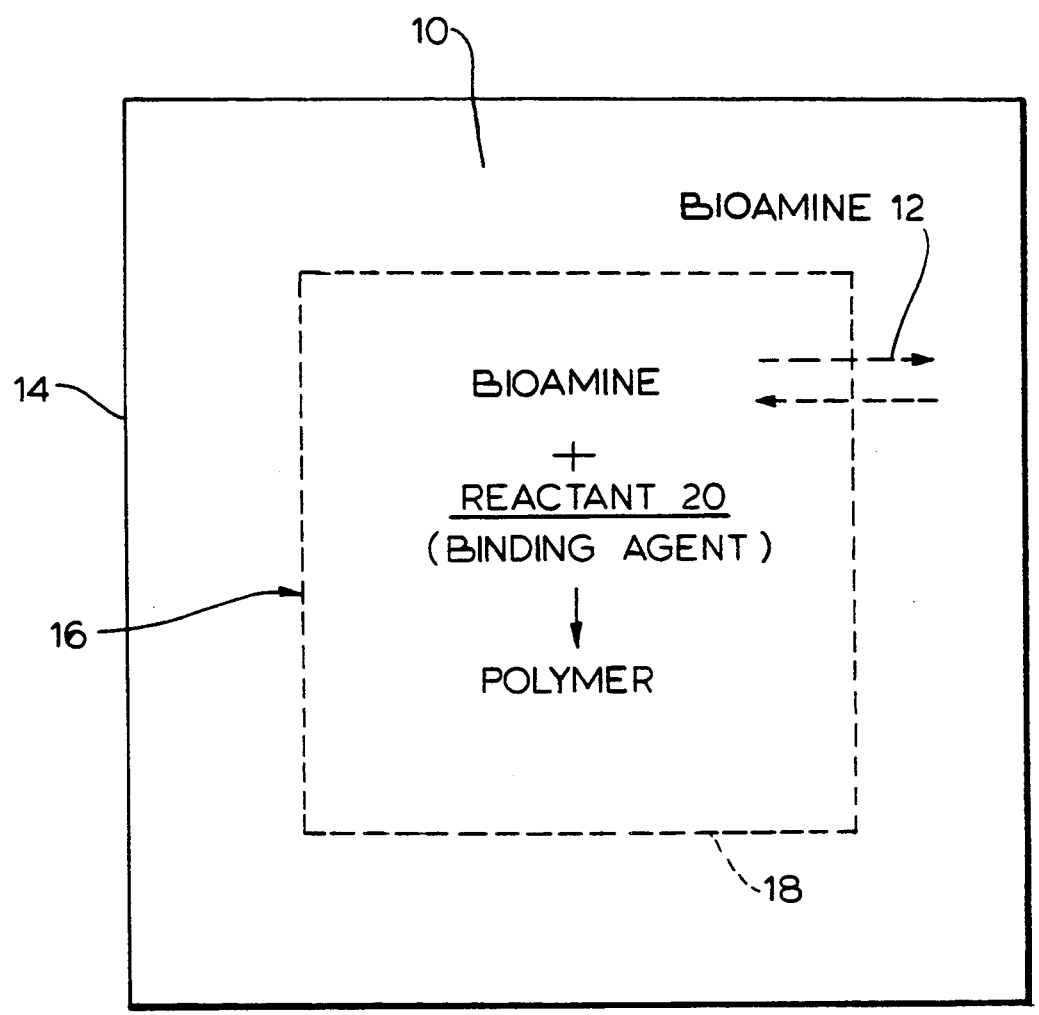

Referring now to FIG. 1D therein illustrated is a schematic of the first embodiment of the present invention for the removal of bioamines 12 from the aliment 10 using binding agents 20. The reaction products formed—primarily polymeramine complexes—are non-diffusible through the membrane 18 and thus remain trapped within the container 16.

It will be appreciated by those skilled in the art that the aliment 10 may include as its impurity 12 carbamates, sulfites, bioamines and combinations thereof. Similarly, the container 16 may include as its reactants 20 the binding agent, neutralizing agent and/or oxidizing agent for the treatment of the sulfites, the transesterifying agent and/or hydrolyzing agent for the treatment of the carbamates, the binding agent for the treatment of bioamines, and combinations thereof.

Figure 2A:
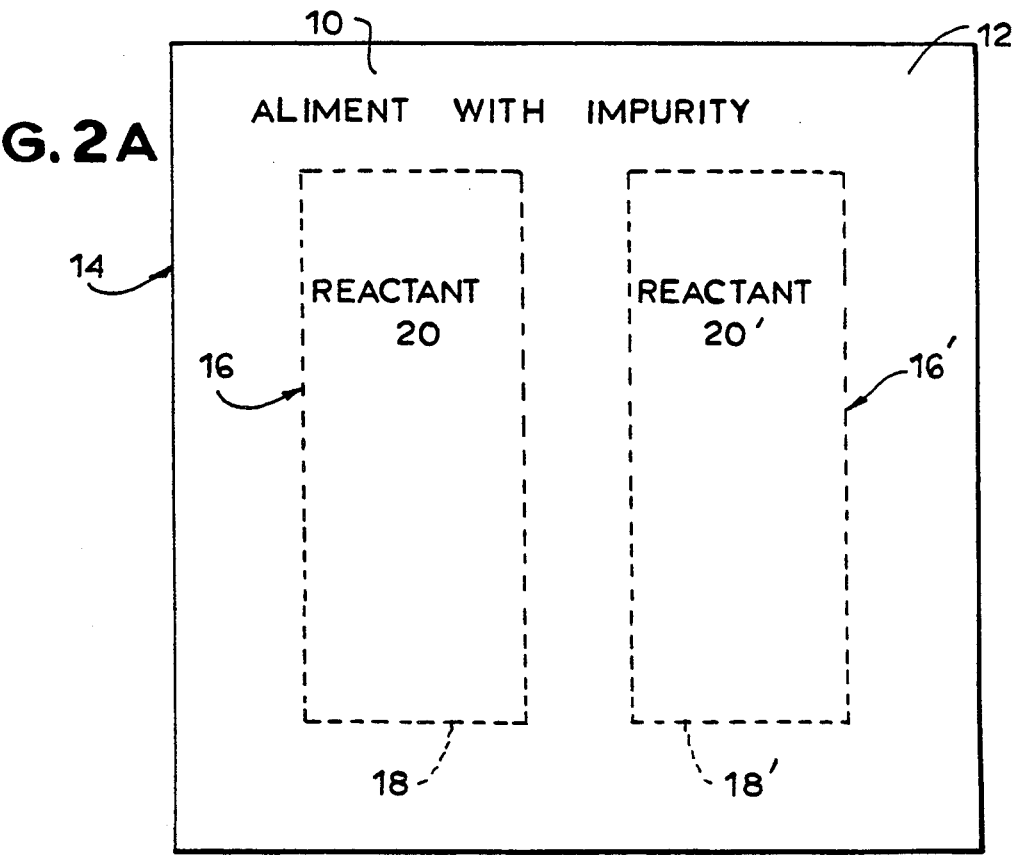
FIG. 2A is a general schematic view of a second embodiment of the present invention wherein there are two separate or dual compartments within the vessel.

Referring now to FIG. 2A, therein illustrated is a general schematic of the second or "dual containers in a vessel" embodiment of the present invention. The second embodiment differs from the first embodiment in that, instead of a single container 16 formed by a membrane 18 within the vessel, there are two separate containers, a first container 16 and a second container 16'. The first container 16 is defined by the membrane 18 and encloses at least one reactant 20, while the second container 16' is defined by the membrane 18' and encloses at least one reactant 20'. For particular applications, the membranes 18, 18' may be of the same type, and the reactants 20, 20' may be the same. The increased surface area provided by two containers 16, 16' as opposed to only one container 16 will enable the impurities to be removed with greater speed as a result of two containers being operative simultaneously. Alternatively, the two containers 16, 16' within the vessel 14 may be disposed so that the aliment 10 passes sequentially through the containers 16, 16'.

While carbamates are desirably removed at any stage in the production of an alcoholic beverage in advance of consumption (since the carbamate serves no desirable function), by way of contrast, the removal of sulfites from liquids, foods, drugs, etc. is often best performed by the consumer immediately or shortly before consumption, as the sulfite performs various desirable functions prior to that time—namely, preservation and color stabilization. Accordingly, referring now to FIG. 2B, the vessel 14 of the second embodiment may be disposed as an exchanger affixed to a wine bottle, and the aliment 10 containing the impurity 12 poured through the exchanger 14, perhaps as part of decantation or pouring of the wine or other beverage from the wine bottle 20 into a wine glass 32. Thus the aliment 10 sequentially contacts or passes through the containers 16, 16', and the removal of the sulfites therefrom by the reactants 20, 20' within the containers is performed during pouring and therefore presumably just prior to drinking of the beverage. In this case the containers must include sufficient reactant to ensure that all of the impurity is removed by a single pass of the beverage through the exchanger, and, as speed of removal is critical, a sequential disposition of container 16, 16' is desirable. The exchanger would be disposable after a single use or regeneratable. The exchanger may be in the form of a filter (i.e., an impregnated membrane), an impregnated sponge, an impregnated or non-impregnated hollow fiber device, an impregnated baffle, etc.

Referring now to FIG. 2C, therein illustrated is a schematic of the second embodiment for the removal of both sulfites and carbamates (as impurities 12) from an aliment 10. Container 16 is used for removal of carbamates and thus contains as the reactant 20 a transesterifying and/or hydrolyzing agent. The breakdown products carbon dioxide and ethyl alcohol can diffuse through the membrane 18, while the polymer and the breakdown product ammonia are trapped within the container 16, the polymer being non-diffusible through the membrane 18 and the ammonia either being trapped by the strong acid hydrolyzing agent or a special trapping agent also enclosed by the container 16. The container 16' is used for the removal of sulfites and thus contains as the reactant 20' a binding, neutralizing and/or oxidizing agent. The possible reaction products—polymers and sulfate—are trapped by the membrane 18' forming the second container 16'. Sulfite removal is preferably performed in a container 16' having a hydrophobic membrane 18', but the carbamate may be removed in a container 16 having either a hydrophobic or a hydrophilic membrane 18.

The use of separate containers 16, 16' within the vessel 14 enables the aliment 10 to receive treatment by reactants 20 and 20' which might be incompatible if they were present within the same container. Thus the second embodiment may be used to provide removal of even a single impurity 12, but with the reactants 20 and 20' being incompatible for use in the same container.

Fish naturally contains bioamines and additional post-mortem-derived bioamines (from autolysis and bacterial action during processing) and has sulfites added thereto for preservation purposes prior to freezing. Accordingly, one compartment may include a binding agent which is a non-diffusible polymeric strong acid as the reactant in one compartment to remove bioamines and a strong basic agent or a polyaldehyde in the other compartment to remove sulfites. Alternatively, the acid resin and polyaldehyde may be in the same compartment.

Referring now to FIG. 3A, therein illustrated is a general schematic of the third or "stacked containers in a vessel" embodiment of the present invention. Whereas in the second embodiment the two separate chambers 16, 16' are mutually exclusive and separately disposed within the vessel 14, in the third embodiment of the present invention the first chamber 16 (defined by its membrane 18) is physically disposed within the second chamber 16' (defined by membranes 18 and 18'), the second chamber 16' within the third chamber 16", and the third chamber 16" (defined by membrane 18' and vessel 14) within the vessel 14. While there are thus three compartments 16, 16', 16", one of the compartments will be used for the aliment 10, thus leaving only two compartments for containing reactants.

Referring now to FIG. 3B, therein illustrated is a schematic of the third embodiment for the removal of carbamates using two incompatible reactants—namely, a basic hydrolytic agent and an acidic hydrolytic agent—which would neutralize each other if they were disposed within the same container. Thus the first container 16 encloses a basic hydrolyzing agent as its reactant 20; the second container 16' encloses an acidic hydrolytic agent as its reactant 20'; and the third compartment 16" contains the aliment 10 with the carbamate impurity 12. The basic hydrolytic agent serving as reactant 20 decomposes the carbamate, with the formation of carbon dioxide ethanol and ammonium ion. The carbon dioxide and ethanol can diffuse through the membrane 18, 18' and have no adverse effect on the aliment 10. On the other hand, the ammonium ion can also pass through these membranes 18, 18' and would have an adverse effect on the aliment 10. However, within the second container 16' the acidic hydrolytic agent serving as reactant 20' not only cooperates with the basic hydrolytic agent in the decomposition of the carbamates, but also traps the ammonium ion without regard to whether the ammonium ion results from the decomposition which it has initiated or the decomposition initiated in compartment 16 by the basic hydrolytic agent. For this reason, the acid hydrolyzing agent is preferably placed in the outer compartment 16' and the basic hydrolytic agent is placed within the inner compartment 16. Both membranes 18, 18' may be hydrophilic or hydrophobic, and, if desired, they may be of different types. Hydrophobic membranes are required where the strong acids and bases are in the form of low molecular weight compounds.

Figure 3C:
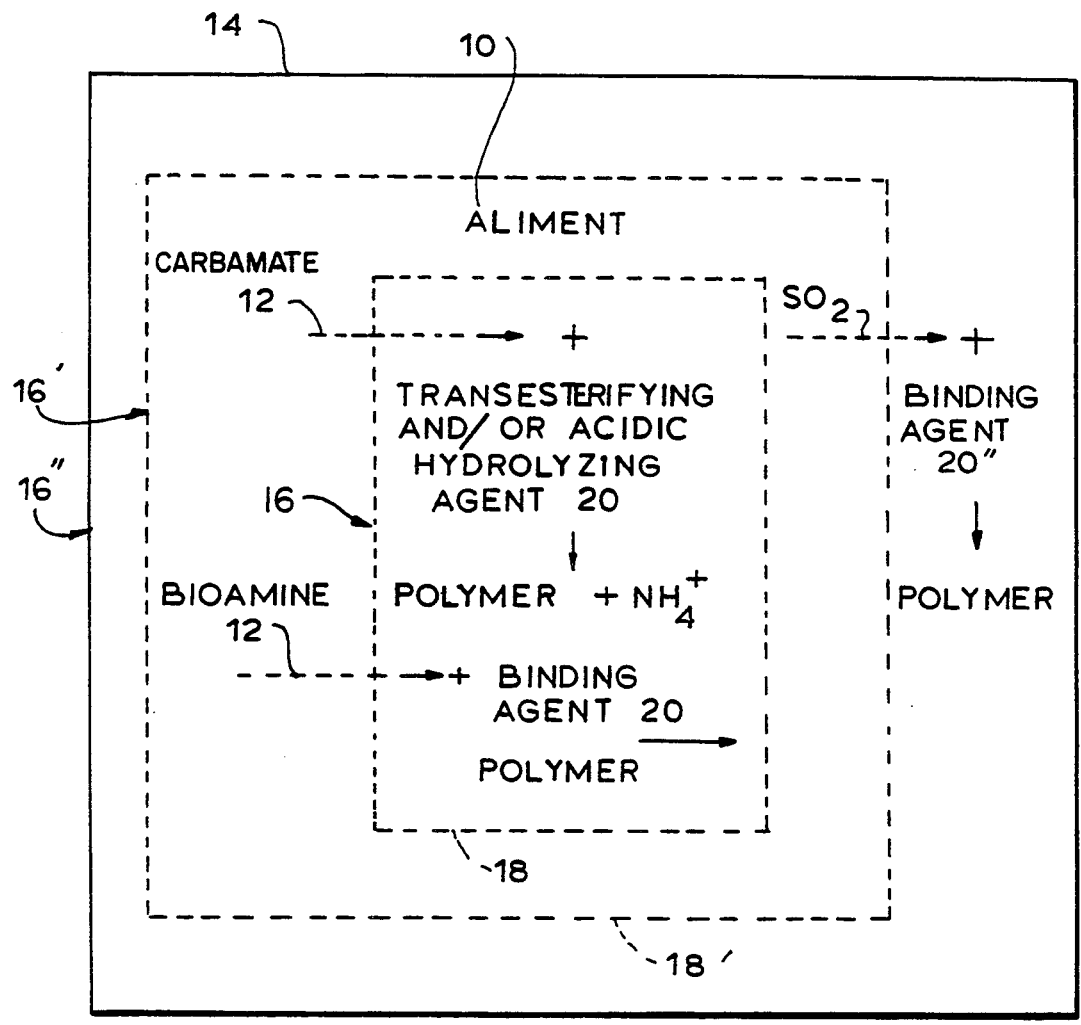
FIG. 3C is a schematic view illustrating the use of the third embodiment to remove carbamates, sulfites, and bioamines.

Referring now to FIG. 3C, therein illustrated is a schematic of the third embodiment for the removal of carbamates, sulfites and bioamines. The aliment 10 containing the impurities 12 (carbamates, sulfites and bioamines) is disposed in the second compartment 16' intermediate the inner or first compartment 16 and the outer or second compartment 16". The inner or first compartment 16 encloses transesterifying and/or acid hydrolyzing agents as the reactants 20 for reaction with the carbamates 12, and a binding agent as the reactant 20 for reaction with the bioamines 12. Both the transesterifying and binding reactions produce modified polymers which are retained within the first compartment 16, while the hydrolyzing reaction gives rise to ammonium ion which is trapped by the acid hydrolyzing agent and therefore cannot escape the container 16. The outer or third compartment 16" encloses a binding agent as the reactant 20" for reaction with the sulfites 12. The reaction product is a polymer which cannot diffuse through the membrane 18' and thus reach aliment 10. Preferably the membrane 18 forming compartment 16 is hydrophobic, and the membrane 18' dividing the second and third compartments 16', 16" is hydrophilic. In particular instances, it may be preferred to have both membranes hydrophobic.

Where it is desired to remove carbamates, sulfites and bioamines from the same beverage, this can be accomplished either simultaneously or sequentially, depending upon the particular membrane and reactant systems utilized.

It will be appreciated that the purification processes described above result in only the most modest alteration of the aliment. Only minuscule changes occur in the water and alcohol contents.

While the present invention has been described in terms of a fluid-impermeable vessel 14 containing both the aliment 10 having the impurity 12 and any containers 16 or 16, 16' formed of a membrane 18 or 18, 18' enclosing a reactant 20 or 20, 20', alternative embodiments of the present invention are of particular utility for given applications.

Referring now to FIGS. 4A–F, therein illustrated are various alternative embodiments of the structure of the present invention. These structures are particularly adapted for use with substantially solid aliments although, if desired, they may be used with more liquid aliments as well. In each figure, each vessel V is a non-permeable structure for the storage and/or cooking of a food product, and the container C contains the reactant or reactants 20 (not shown). The vessel V may have means for enabling the food to be removed therefrom without contamination from any reactants in the container C. Porous hydrophobic vents P are provided on either the container C, the vessel V, or both, in order to enable the passage therethrough of the expanding gases (ordinarily present therein or developed by the reactions) during heating thereof—e.g., air, steam, $SO_2$, etc. The membranes employed in the structure are either porous membranes $M_1$, as necessary to permit the passage of impurities and their breakdown products between the food product and the container C, or non-porous membranes $M_2$ for physically defining the vessel V and protecting the food product from the environment.

Figure 4A:
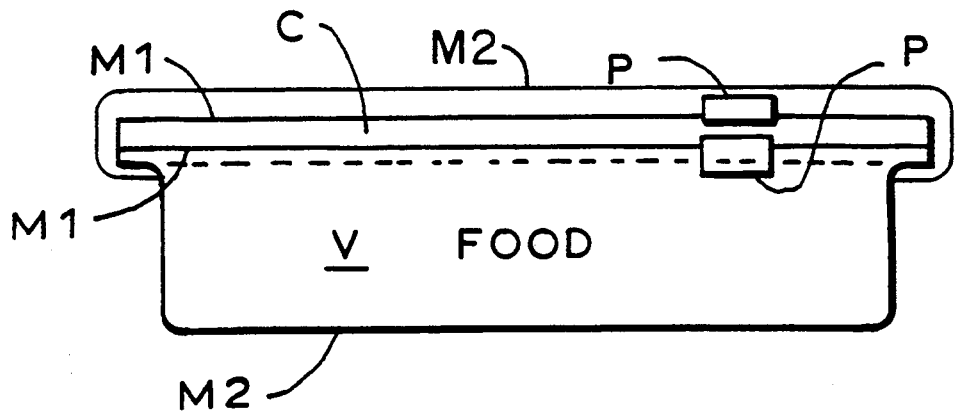
FIGS. 4A-4F are schematics of alternative structures according to the present invention.

Referring now to FIG. 4A, therein illustrated is a vessel V in the form of a non-permeable pan or tray having an open top, such as the conventional tray for the oven cooking of frozen food. The open top of the tray is covered with a removable non-permeable membrane $M_2$ (usually removed before cooking) and typically contains a frozen food. A container C is disposed on the vessel V, below the membrane $M_2$, so as to removably close the open top of the vessel V. The container C is defined by the permeable membrane $M_1$ and contains the appropriate reactant or reactants for removal of impurities from the food within the vessel V. Porous hydrophobic vents are provided on both the upper and lower surfaces of the container C. It will be appreciated that in this embodiment the container C is adjacent to, but not within, the vessel V.

Figure 4B:
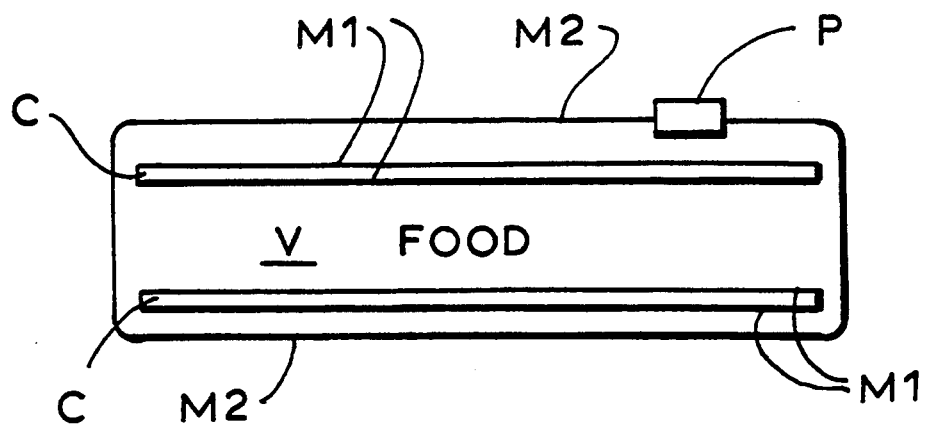
Figure 4C:
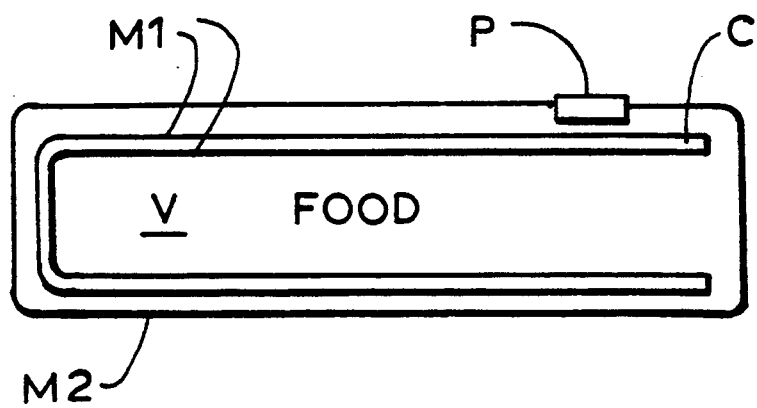

Referring now to FIG. 4B, therein illustrated is a structure particularly well suited for frozen foods, such as frozen vegetables. The vessel V contains both a food product and at least one container C, the vessel being formed of the non-porous membrane $M_2$ and each container C being formed of the porous membrane $M_1$. The vessel V additionally defines at least one porous hydrophobic vent. It will be appreciated that the food product does not have to be encased in any particular packaging or membrane other than the membrane $M_2$ of the vessel V. The two illustrated containers are preferably disposed of, with the vessel V, after the food products have been removed from the vessel V. While two separate and distinct containers have been illustrated, the structure may be operated with only a single container C unless there is a reason for using two separate and distinct containers (for example, to separate incompatible reactants in their respective containers C). As illustrated in FIG. 4C, where only a single container C is employed within the vessel V, the container C is preferably of a U-shaped configuration so as to maintain intimate contact with a large proportion of the food product while still allowing the food product to be removed from the vessel V without any rupture of the container C. It will be appreciated that the embodiments of FIGS. 4C and 4B are similar in many respects to the general embodiments illustrated in FIGS. 1A and 2A, respectively, the container or containers in each case being disposed within the vessel.

Figure 4D:
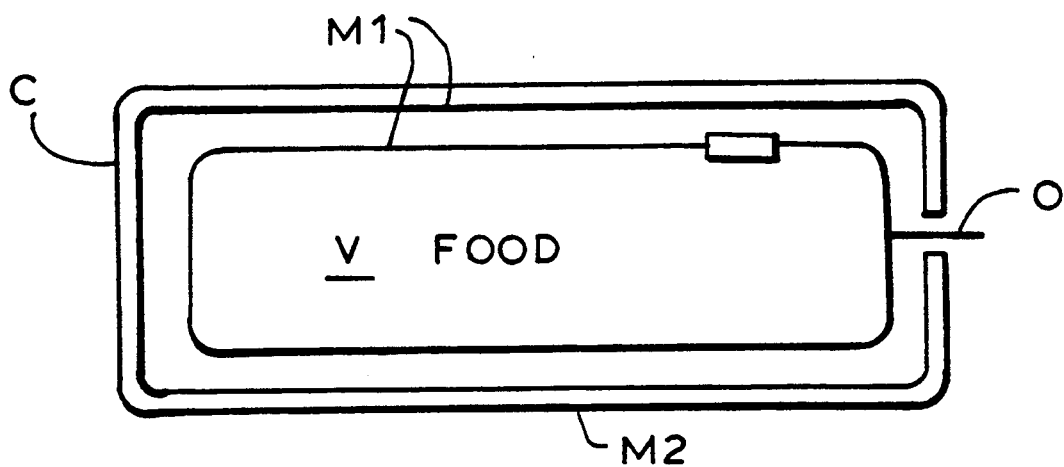

Referring now to FIG. 4D, therein illustrated is an embodiment wherein the vessel V is disposed within the container C. The vessel V is defined by the permeable membrane $M_1$ and contains food. It is in communication with the container C formed by the non-porous membrane $M_2$ (on the outside) and the permeable membrane $M_1$ (on the inside) thereabout through the porous hydrophobic vent P in membrane $M_2$. Preferably the container C does not completely enclose the vessel V, but enables passage therethrough of, or access to, an opening mechanism O so that the food may be removed from the vessel V without tearing of the container C, thereby to avoid contamination of the food product by the reactants within the container C.

Figure 4E:
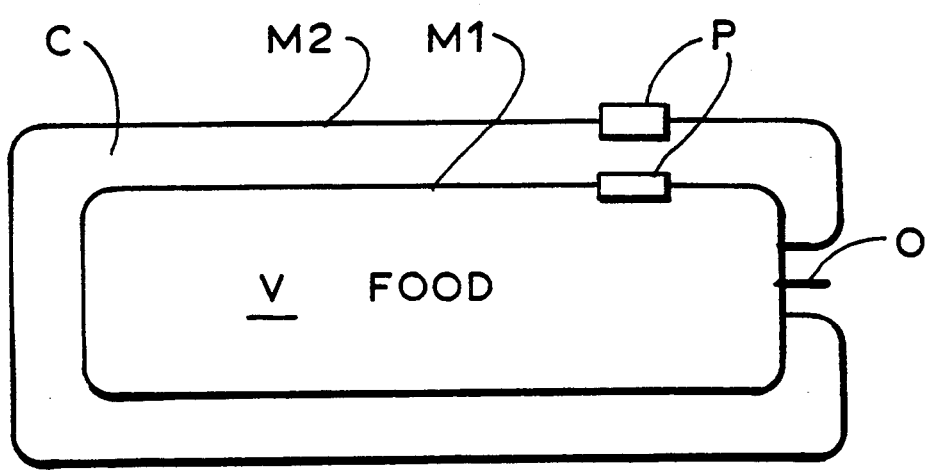
Figure 4F:
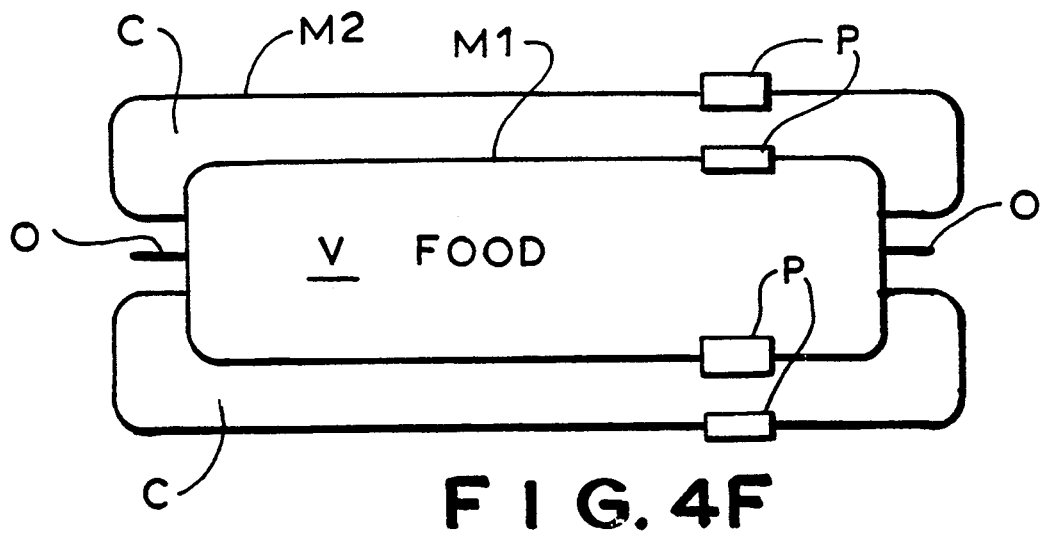

Referring now to FIG. 4E, the vessel V is similar to the vessel V of FIG. 4D, defining an opening mechanism O at one end and containing food. However, the vessel V here defines a portion of the container C thereabout and thus is formed from a porous membrane $M_1$. Accordingly, the outer surface of the container C is formed of a non-porous membrane $M_2$, while the inner surface thereof (defined by the wall of the vessel V) is defined by a porous membrane $M_1$, both membranes $M_1$, $M_2$ defining porous hydrophobic vents P therethrough. Whereas in FIG. 4D, communication between the vessel and the container is limited to passage via the porous hydrophobic vent P on the vessel wall, the entire vessel wall $M_1$ permits communication between the food product in the vessel V and the reactants in the container C. Whereas in FIG. 4E the container C is U-shaped with the legs approaching in the vicinity of the opening mechanism O, in FIG. 4F there are two separate compartments C with opening mechanisms O at each end of the vessel V. This embodiment permits incompatible reagents to be disposed within respective compartments C.

It will be appreciated that FIGS. 4A–F are only representative of the various vessel/container structures which may be used to enable the removal of impurities from the food by means of reactants enclosed within the container.

It will further be appreciated that the relative sizes of the vessel V and the compartments 16, 16', 16'' are not drawn to scale in FIGS. 1–4.

The system of the present invention has been described hereinabove in terms of a "closed" or "batch" system wherein the vessel 14 and container 16 are closed and contained a fixed quantity of aliment 10 or reactant 20. Even in the system of FIG. 2B, while a variable amount of wine may flow from the wine bottle 30 into the wine glass 32, the quantity of reactants 20' is fixed. However, commercial manufacturing processes are preferably of a "continuous" nature. Accordingly, the principles of the present invention apply equally to systems wherein one or both of the vessel and container are open ended so that there is a continuous flow therethrough of its (their) respective contents. Thus, the aliment 10 containing the impurity 12 may flow through the vessel 14 on a continuous basis, while the reactant 20 is flowing through the container 16 on a continuous basis in either the same direction or a different direction. Thus, for the purposes of the present invention, the terms "vessel" and "container" are used broadly and encompass conduits for liquid flows where the conduits are separated by an appropriate membrane 18.

To summarize, the present invention provides a method for improving the quality of an aliment by removing an impurity therefrom and, in particular, a method for improving the quality of an alcoholic liquor by removing an impurity selected from the group consisting of carbamates, sulfites, bioamines, and combinations thereof. The method economically removes the impurities without degrading the quality of the aliment.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

We claim:

1. A method for improving the quality of an aliment by removing therefrom an impurity selected from the group consisting of carbamates, sulfites, bioamines, and combinations thereof, comprising the steps of:
   (A) contacting an aliment containing an impurity selected from the group consisting of carbamates, sulfites, bioamines and combinations thereof, with a container formed of a membrane permeable to the impurity and its breakdown products and enclosing a reactant non-diffusible through the membrane and selected from the group consisting of:
      (i) a binding agent,
      (ii) a neutralizing agent,
      (iii) an oxidizing agent,
      (iv) a transesterifying agent,
      (v) a hydrolyzing agent, and
      (vi) combinations thereof; and
   (B) separating the container and the contents thereof from the aliment after a period of time sufficient for the reactant to react with the impurity.

2. The method of claim 1 wherein the container further encloses an antioxidant.

3. A method for improving the quality of an aliment by removing therefrom sulfites, comprising the steps of:
   (A) contacting an aliment containing sulfites with a container formed of a membrane permeable to sulfites and enclosing a non-diffusible reactant selected from the group consisting of:
      (i) a binding agent including a non-diffusible polymeric aldehyde for binding sulfites into a non-diffusible polymer,
      (ii) a neutralizing agent including a non-diffusible polymeric base for neutralizing sulfites,
      (iii) an oxidizing agent including a non-diffusible peroxide for oxidizing sulfites to sulfate, and
      (iv) combinations thereof; and (B) separating the container and the contents thereof from the aliment after a period of time sufficient for the reactant to react.

4. The method of claim 3 wherein the container further encloses an antioxidant.

5. The method of claim 4 wherein said antioxidant includes a non-diffusible polymeric phenol for maintaining the reduced forms of natural phenols.

6. A method for improving the quality of an aliment by removing therefrom carbamates, comprising the steps of:
  (A) contacting an aliment containing carbamate with a container formed of a membrane permeable to carbamate and enclosing a non-diffusible reactant selected from the group consisting of:
    (i) a transesterifying agent including a non-diffusible polymer containing hydroxyphenyl moieties for reacting with carbamates to form non-diffusible hydrolyzable aryl esters of carbamic acid,
    (ii) an acidic hydrolyzing agent including a non-diffusible strongly acidic polymer for hydrolyzing carbamates and binding the ammonia and amines by-products,
    (iii) a basic hydrolyzing agent including a non-diffusible strongly basic polymer for hydrolyzing carbamates,
    (iv) an enzymatic hydrolyzing agent including a non-diffusible esterolytic enzyme, and
    (v) combinations thereof; and
  (B) separating the container and the contents thereof from the aliment after a period of time sufficient for the reactant to react.

7. A method for improving the quality of an aliment by removing therefrom bioamines, comprising the steps of:
  (A) contacting an aliment containing bioamines, with a container formed of a membrane permeable to bioamines and enclosing a non-diffusible reactant which is a binding agent selected from the group consisting of a non-diffusible polymeric aldehydes, non-diffusible strongly acidic polymers and combinations thereof for binding bioamines into a non-diffusible polymer; and
  (B) separating the container and the contents thereof from the aliment after a period of time sufficient for the reactant to react.

8. A system for improving the quality of an aliment by removing therefrom at least one impurity selected from the group consisting of carbamates, sulfites and bioamines, comprising:
  (A) a liquid-impermeable vessel enclosing an aliment containing an impurity selected from the group consisting of carbamates, sulfites, bioamines and combinations thereof; and
  (B) in fluid communication with the aliment, a container formed of a membrane permeable to the impurity and its breakdown products and enclosing a reactant non-diffusible through the membrane and selected from the group consisting of:
    (i) a binding agent,
    (ii) a neutralizing agent,
    (iii) an oxidizing agent,
    (iv) a transesterifying agent,
    (v) a hydrolyzing agent, and
    (vi) combinations thereof.

9. A system for improving the quality of an aliment by removing therefrom sulfites, comprising:
  (A) a liquid-impermeable vessel enclosing an aliment containing sulfites; and
  (B) in fluid communication with the aliment, a container formed of a membrane permeable to sulfites and enclosing a non-diffusible reactant selected from the group consisting of:
    (i) a binding agent including a non-diffusible polymeric aldehyde for binding sulfites into a non-diffusible polymer,
    (ii) a neutralizing agent including a non-diffusible polymeric base for neutralizing sulfites,
    (iii) an oxidizing agent including a non-diffusible peroxide for oxidizing sulfites to sulfates, and
    (iv) combinations thereof.

10. A system for improving the quality of an aliment by removing therefrom carbamates, comprising:
  (A) a liquid-impermeable vessel enclosing an aliment containing carbamate; and
  (B) in fluid communication with the aliment, a container formed of a membrane permeable to carbamate and enclosing a non-diffusible reactant selected from the group consisting of:
    (i) a transesterifying agent including a non-diffusible polymer containing hydroxyphenyl moieties for reacting with carbamates to form non-diffusible hydrolyzable aryl esters of carbamic acids,
    (ii) an acidic hydrolyzing agent including a non-diffusible strongly acidic polymer for hydrolyzing carbamates and binding the ammonia or amine by-products,
    (iii) a basic hydrolyzing agent including a non-diffusible strongly basic polymer for hydrolyzing carbamates,
    (iv) an enzymatic hydrolyzing agent including a non-diffusible esterolytic enzyme, and
    (v) combinations thereof.

11. A system for improving the quality of an aliment by removing therefrom bioamines, comprising:
  (A) a liquid-impermeable vessel enclosing an aliment containing bioamines; and
  (B) in fluid communication with the aliment, a container formed of a membrane permeable to bioamines and enclosing a non-diffusible reactant which is a binding agent selected from the group consisting of non-diffusible polymeric aldehydes, non-diffusible strongly acidic polymers and combinations thereof for binding bioamines into a non-diffusible polymer.

12. A system for improving the quality of an aliment by removing therefrom at least one impurity, comprising:
  (A) a liquid-impermeable vessel enclosing an aliment containing an impurity; and
  (B) in fluid communication with the aliment, a container formed of a membrane permeable to the impurity and its breakdown products and enclosing a reactant non-diffusible through the membrane and selected from the group consisting of:
    (i) a binding agent,
    (ii) a neutralizing agent,
    (iii) an oxidizing agent,
    (iv) a transesterifying agent,
    (v) a hydrolyzing agent, and
    (vi) combinations thereof.

13. The system of claim 12 including a plurality of said containers, said containers being separate and distinct.

14. The system of claim 13 wherein the reactants of at least two of said plurality of containers are incompatible.

15. The system of claim 12 including a stacked plurality of said containers, an inner one of said containers being disposed entirely within an outer one of said containers.

16. The system of claim 15 wherein the reactants of at least two of said plurality of containers are incompatible.

17. The system of claim 16 wherein said inner container encloses an acidic hydrolyzing agent and said outer container encloses a basic hydrolyzing agent, the membrane intermediate said inner and outer containers being permeable to carbamate, ammonia, amines, carbon dioxide and ethanol.

18. The system of claim 12 wherein said vessel defines an open top, and said container is removably disposed on said vessel to close said open top.

19. The system of claim 12 wherein said container substantially encloses said vessel.

20. The system of claim 19 wherein said vessel defines a porous hydrophobic vent.

21. The system of claim 12 wherein said vessel substantially encloses said container.

22. The system of claim 21 wherein each of said vessel and said container each defines a porous hydrophobic vent.

23. A method for improving the quality of an aliment by removing therefrom an impurity, comprising the steps of:
(A) contacting an aliment containing an impurity with a container formed of a membrane permeable to the impurity and its breakdown products and enclosing a reactant non-diffusible through the membrane and selected from the group consisting of:
   (i) a binding agent,
   (ii) a neutralizing agent,
   (iii) an oxidizing agent,
   (iv) a transesterifying agent,
   (v) a hydrolyzing agent, and
   (vi) combinations thereof; and
(B) separating the container and the contents thereof from the aliment after a period of time sufficient for the reactant to react with the impurity.

* * * * *